(12) United States Patent
Knust et al.

(10) Patent No.: US 8,202,888 B2
(45) Date of Patent: Jun. 19, 2012

(54) PIPERIDINE SULPHONAMIDE DERIVATIVES

(75) Inventors: Henner Knust, Rheinfelden (DE); Matthias Nettekoven, Grenzach-Wyhlen (DE); Emmanuel Pinard, Linsdorf (FR); Olivier Roche, Folgensbourg (FR); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 394 days.

(21) Appl. No.: 12/365,911

(22) Filed: Feb. 5, 2009

(65) Prior Publication Data

US 2009/0203736 A1 Aug. 13, 2009

(30) Foreign Application Priority Data

Feb. 12, 2008 (EP) .................... 08151328

(51) Int. Cl.
  *A61K 31/454* (2006.01)
  *C07D 401/06* (2006.01)
(52) U.S. Cl. ...................... 514/326; 546/208
(58) Field of Classification Search .......... None
  See application file for complete search history.

(56) References Cited

U.S. PATENT DOCUMENTS

| 2004/0215014 | A1 | 10/2004 | Chan et al. | |
| 2005/0288317 | A1* | 12/2005 | Yao et al. | 514/278 |
| 2006/0199816 | A1 | 9/2006 | Gillespie et al. | |

FOREIGN PATENT DOCUMENTS

WO  WO 2007/082840  7/2007

OTHER PUBLICATIONS

Medline Plus, "Autoimmune disorders," National Istitutes of Health. <http://www.nlm.nih.gov/medlineplus/article/000816.htm> Accessed Jun. 3, 2011.*
Siegel, Annu. Rev. Psychol. vol. 55, pp. 125-148 (2004).
Delecea et al., Proc. Natl. Acad. Sci. USA vol. 95 pp. 322-327 (1998).
Sakurai et al., Cell vol. 92, pp. 573-585 (1998).
Sakurai, Regulatory Peptides vol. 126 pp. 3-10 (2005).
Peyron et al., J. Neurosci. vol. 18, pp. 9996-10015 (1998).
Nambu et al., Brain Res. vol. 827 pp. 243-260 (1999).
Chemelli et al., Cell, vol. 98 pp. 437-451 (1999).
Lin et al., Cell. vol. 98 pp. 365-376 (1999).
Nishino et al., Lancet vol. 355 pp. 39-40 (2000).
Peyron et al., Nature Medicine vol. 6 pp. 991-997 (2000).
Mignot et al., Sleep vol. 11 pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Winsky Sommerer et al., J. Neuroscience vol. 24 pp. 11439-11448 (2004).
Chang et al., Neurosci. Res. vol. 56 pp. 356-362 (2006).
Digby et al., J. Endocrinol. vol. 191 pp. 129-136 (2006).
Cai, et al., Expert Opin. Ther. Patents vol. 16(5) pp. 631-646 (2006).
Bourgin et al., J. Neurosci. vol. 20(20) pp. 7760-7765 (2000).
Smith, et al., Neurosci. Lett. vol. 341(3) pp. 256-258 (2003).
Rodriguez et al., Tetrahedron Letters, vol. 25 p. 527-528 (1984). *English language translation attached.*
Walther G., Chem. Ber, vol. 84 p. 304-307 (1951). *English language translation attached.*
Malherbe et al., Mol. Pharmacol. vol. 64 pp. 823-832 (2003).
Database CHEMCATS (2008) Access No. 2042575335, XP002532199.
Database CHEMCATS (2008) Access No. 204671585, XP002532200.
Database CHEMCATS (2008) Access No. 2042645531, XP002532201.
Database CHEMCATS (2008) Access No. 2042576330, XP002532202.
Database CHEMCATS (2008) Access No. 2042554852, XP002532203.
Database CHEMCATS (2008) Access No. 2042553638, XP002532204.
Database CHEMCATS (2008) Access No. 20425522338, XP002532205.
Database CHEMCATS (2008) Access No. 2042551562, XP002532206.
Database CHEMCATS (2008) Access No. 2042551010, XP002532207.
Database CHEMCATS (2008) Access No. 2042549836, XP002532208.
Database CHEMCATS (2008) Access No. 2042549684, XP002532209.

* cited by examiner

*Primary Examiner* — Rebecca Anderson
*Assistant Examiner* — Alicia L Otton
(74) *Attorney, Agent, or Firm* — George W. Johnston; Patricia S. Rocha-Tramaloni; Kimberly J. Prior

(57) ABSTRACT

The present invention relates to piperidine sulphonamide derivatives of formula

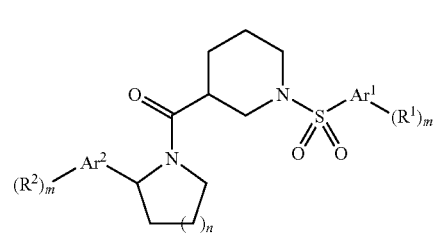

wherein $Ar^1$, $Ar^2$, $R^1$, $R^2$, m and n are as defined in the description and claims, or pharmaceutically suitable acid addition salts thereof. The compounds of formula I are orexin receptor antagonists and the related compounds can be useful in the treatment of sleep apnea, narcolepsy, insomnia, parasomnia, jet lag syndrome, circadian rhythms disorder or sleep disorders associated with neurological diseases.

7 Claims, No Drawings

PIPERIDINE SULPHONAMIDE DERIVATIVES

PRIORITY TO RELATED APPLICATION(S)

This application claims the benefit of European Patent Application No. 08151328.5, filed Feb. 12, 2008, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX-B was observed in human narcoleptic patients (Nishino et al., *Lancet*, 355, 39-40, 2000; Peyron et al., Nature Medicine, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracerebroventricular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R (N-{(1S)-1-(6,7-dimethoxy-3,4-dihydro-2(1H)-isoquinolinyl) carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipsychotics, and other diseases related to general orexin system dysfunction.

Numerous documents describe the current knowledge on orexin pathway, for example the following documents:

Expert Opin. Ther. Patents (2006), 16(5), 631-646
Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention provides compounds of formula I

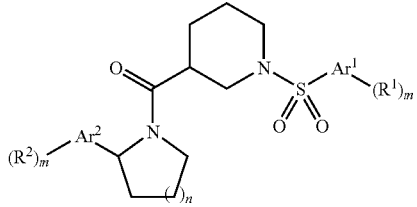

wherein
- $Ar^1$ and $Ar^2$ are each independently unsubstituted or substituted aryl or heteroaryl;
- $R^1$ and $R^2$ are each independently hydroxy, halogen, lower alkyl, lower alkyl substituted by halogen, lower alkoxy, lower alkoxy substituted by halogen or cyano;
- m is 0, 1, 2 or 3; and
- n is 1 or 2;

or to pharmaceutically suitable acid addition salts thereof.

Compounds of formula I are orexin receptor antagonists and related compounds may be useful in the treatment of disorders in which orexin pathways are involved, like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipschotics and other diseases related to general orexin system dysfunction.

DETAILED DESCRIPTION OF THE INVENTION

The following definitions of the general terms used in the present description apply irrespective of whether the terms in question appear alone or in combination.

As used herein, the term "alkyl" denotes a straight- or branched-chain hydrocarbon group containing from 1-7 carbon atoms. The term "lower alkyl" denotes a straight- or branched-chain hydrocarbon group containing from 1-4 carbon atoms, for example, methyl, ethyl, propyl, ethyl, propyl, isopropyl, n-butyl, i-butyl, t-butyl and the like.

The term "halogen" denotes chlorine, iodine, fluorine and bromine.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "lower alkoxy" denotes an alkyl group as defined above, which is attached via an oxygen atom.

The term "lower alkoxy substituted by halogen" denotes an alkoxy group as defined above in which at least one hydrogen atom on the alkyl group is replaced by halogen.

The term "aryl" means the monovalent cyclic aromatic hydrocarbon group having 5 to 20 ring carbon atoms and consisting of one or more fused rings in which at least one ring is aromatic in nature. Examples of aryl radicals include, but are not limited to, phenyl, naphthyl, 5,6,7,8-tetrahydro-naphthalenyl, biphenyl, indanyl, anthraquinolyl, and the like.

"Heteroaryl" means a cyclic group having one or more rings, wherein at least one ring is aromatic in nature, that has 5 to 20 ring atoms and incorporates one, two, or three heteroatoms within the ring (chosen from nitrogen, oxygen, and sulfur). Examples of heteroaryl radicals include, but are not limited to, imidazolyl, oxazolyl, isoxazolyl, thiazolyl, thiophenyl, furanyl, pyrazolyl, pyridinyl, pyrazinyl, pyrimidinyl, pyridazinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, chromanyl, naphtyridinyl, 2,3-dihydro-benzofuranyl, 3,4-dihydro-2H-benzo[b][1.4]dioxepinyl, 3,4-dihydro-2H-benzo[1.4]oxazinyl, indanyl, benzo[1.3]dioxol, 2,3-dihydro-benzo[1.4]dioxinyl, and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those wherein n is 1.
Preferred compounds from this group are for example the following compounds
- [1-(2-chloro-benzenesulfonyl)-piperidin-3-yl]-[2-(4-fluoro-phenyl)-pyrrolidin-1-yl]-methanone;
- [1-(2-chloro-benzenesulfonyl)-piperidin-3-yl]-(2-phenyl-pyrrolidin-1-yl)-methanone;
- [1-(3-chloro-benzenesulfonyl)-piperidin-3-yl]-(2-phenyl-pyrrolidin-1-yl)-methanone;
- [1-(2-methoxy-benzenesulfonyl)-piperidin-3-yl]-(2-phenyl-pyrrolidin-1-yl)-methanone
- [1-(5-Chloro-2-methoxy-benzenesulfonyl)-piperidin-3-yl]-(2-phenyl-pyrrolidin-1-yl)-methanone; and
- [1-(2-chloro-benzenesulfonyl)-piperidin-3-yl]-[2-(2-chloro-phenyl)-pyrrolidin-1-yl]-methanone.

Preferred compounds of formula I are further those wherein n is 2.

Preferred compounds from this group are for example the following compounds [1-(2-methoxy-benzenesulfonyl)-piperidin-3-yl]-(2-phenyl-piperidin-1-yl)-methanone and [1-(5-chloro-2-methoxy-benzenesulfonyl)-piperidin-3-yl]-(2-phenyl-piperidin-1-yl)-methanone.

Also preferred are compounds where $Ar^1$ is phenyl or compounds where $Ar^1$ is heteroaryl.

Also preferred are compounds where Ar² is phenyl or compounds where Ar² is heteroaryl.

Preferred are compounds where m is 0. Also preferred are compounds where m is 1. Other preferred compounds are those where m is 2; also preferred are compounds where m is 3.

The present compounds of formula I and their pharmaceutically acceptable salts can be prepared by methods known in the art, for example, by processes described below, which process comprises
a) reacting a compound of formula

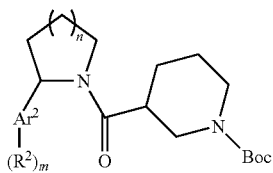

III with a corresponding sulfonylchloride of formula

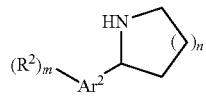

VII to obtain a compound of formula

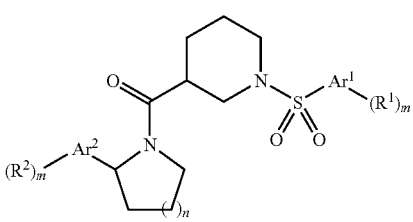

I wherein Ar¹, Ar², R¹, R², m and n are as described above, or
b) reacting a compound of formula

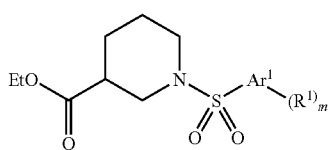

V with a corresponding compound of formula

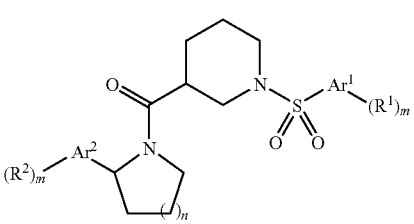

VI to obtain a compound of formula

I wherein Ar¹, Ar², R¹, R², m and n are as described above, and
if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1 method A

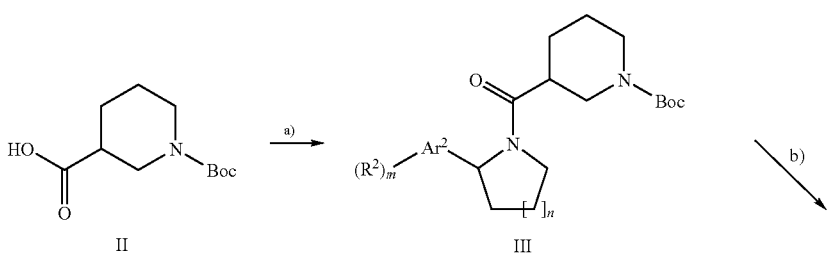

II                III

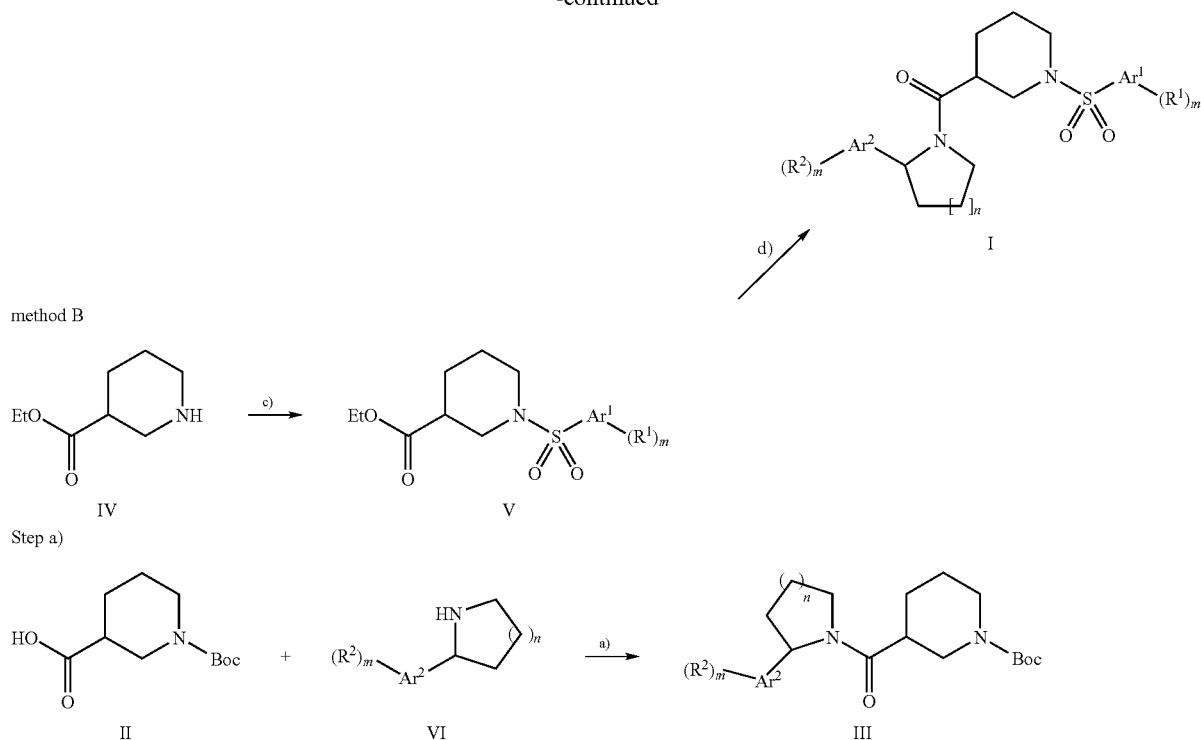

method B

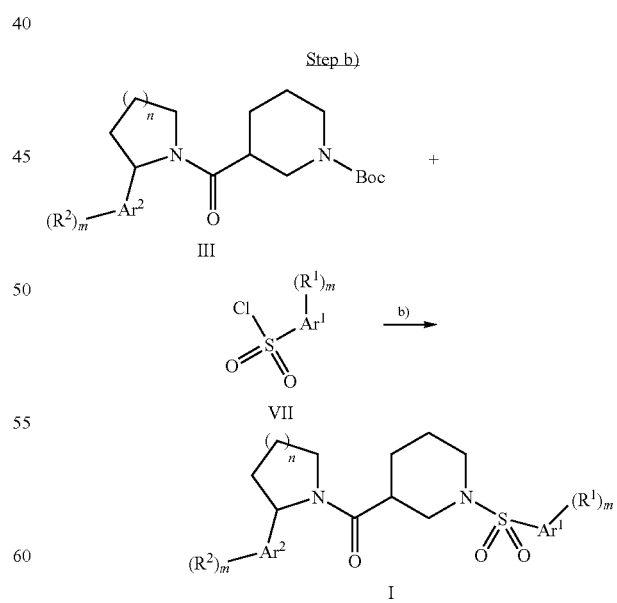

Step a)

1-(tert-Butoxycarbonyl)-3-piperidinecarboxylic acid II is commercially available and can be coupled with 2-phenyl pyrrolidines or piperidenes VI, which are commercially available or can be accessed by methods described in literature like in: Basha, F. Z.; Debernardis, J. F.; Tetrahedron Lett 1984, 25, 527 or Walter, G.; Chem Ber 1951, 84, 304. In general the coupling of carboxylic acids with amines is widely described in literature and the procedures are known to those in the art (For reaction conditions described in literature affecting such reactions see for example: Comprehensive Organic Transformations: A Guide to Functional Group Preparations, $2^{nd}$ Edition, Richard C. Larock. John Wiley & Sons, New York, N.Y. 1999). The acid can conveniently be transformed to the respective amide through coupling with an amine by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. It is convenient to carry out the reaction in a solvent and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield protected amide III.

The removal of a Boc-protecting group is widely described in literature. For examples affecting such a transformation see for example: Comprehensive Organic Transformations: A Guide to Functional Group Preparations, $2^{nd}$ Edition, Richard C. Larock. John Wiley & Sons, New York, N.Y. 1999. However, we find it convenient to react the protected amide III with acid in a solvent. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the acid used in this stage, and any acid commonly used in this type of reaction can equally be employed here. Examples of such acids include TFA and HCl, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the free amine which can be coupled with sulfonylchlorides VII (either commercially available or accessible through methods described in literature) in the literature) in the presence of a base and a solvent to yield the piperidine sulfonamides I. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield piperidine sulfonamides I.

Step c)

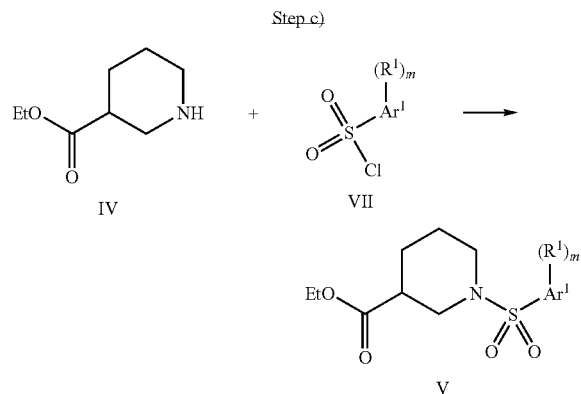

Piperidine-3-carboxylic acid ethyl ester IV is commercially available and can be coupled with sulfonylchlorides VII (either commercially available or accessible through methods described in literature) in the presence of a base and a solvent to yield the piperidine uspend mide ester V. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending required for the reaction can also vary widely, depending on many factors, notably the reaction temperature and the nature of the reagents. However, a period of from 0.5 h to several days will usually suffice to yield piperidine uspend mide ester V.

Step d)

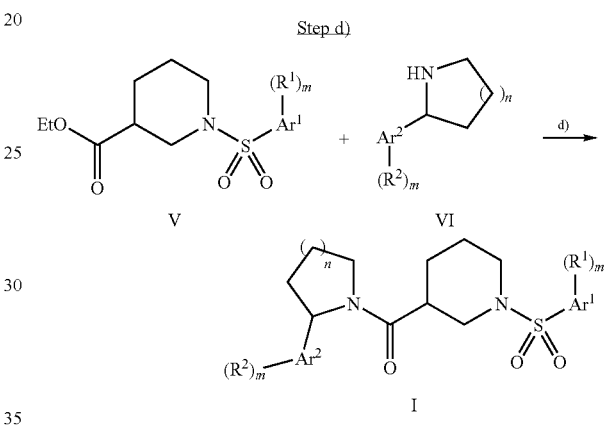

Piperidine sulfonamide ester V can be transformed to the final piperidine sulfonamides I in analogy to procedures described in literature. However, we find it convenient to employ a two step reaction sequence in which the ester functionality in V is cleaved under aqueous basic conditions and the liberated acid functionality converted with the respective amines VI under coupling conditions. There is no particular restriction on the nature of the aqueous base to be employed, provided that it has no adverse effect on the reaction or the reagents involved and that it can dissolve the reagents, at least to some extent. Examples for suitable aqueous bases include NaOH, LiOH and the like. Any commonly used co-solvent can be employed. Examples include methanol, THF water, and the like. The coupling of carboxylic acids with amines is widely described in literature and the procedures are known to those in the art (For reaction conditions described in literature affecting such reactions see for example: Comprehensive Organic Transformations: A Guide to Functional Group Preparations, $2^{nd}$ Edition, Richard C. Larock. John Wiley & Sons, New York, N.Y. 1999). The intermediately built acid can conveniently be transformed to the respective amide through coupling with an amine VI (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'- tetramethyluronium tetrafluoroborate (TBTU) and the like can equally well be employed to affect such transformation. We find it convenient to carry out the reaction in a solvent and in the presence of a base. There is no particular restriction on the nature of the solvent to be employed, provided that it has no adverse effect on the reaction or the reagents involved and involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield piperidine sulfonamides I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1×) with GlutaMax™1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 µg/ml penicillin and 100 µg/ml streptomycin. The cells were seeded at $5 \times 10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 µM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No. 1455, Toris Cookson Ltd, Bristol, UK) was used as agonist. Orexin A (50 mM stock solution in DMSO) was diluted in FLIPR buffer+0.1% BSA. The $EC_{50}$ and $EC_{80}$ values of orexin-A were measured daily from standard agonist concentration-response curves in CHO(dHFr-)-OX1R and -OX2R cell lines. All compounds were dissolved in 100% DMSO. Inhibition curves were determined by addition of 11 concentrations (0.0001-10 µM) of inhibitory compounds and using $EC_{80}$ value of orexin-A as agonist (a concentration which gave 80% of max agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{n_H})$, where $n_H$=slope factor using Excel-fit 4 software (Microsoft).

$K_b$ values were calculated according to the following equation $K_b=IC_{50}/(1+[A]/EC_{50})$ where A is the concentration of agonist added which is very close to agonist $EC_{80}$ value, and $IC_{50}$ and $EC_{50}$ values were derived from the antagonist inhibition and orexin-A or B agonist curves, respectively.

The compounds show a $K_b$ value (µM)<0.1 in human on orexin receptor as shown in the table below.

| Example | $K_b$ (µM) OX2R (human) |
| --- | --- |
| 3 | 0.0788 |
| 7 | 0.02 |
| 8 | 0.0219 |
| 10 | 0.0226 |
| 11 | 0.0053 |
| 14 | 0.0138 |
| 16 | 0.0592 |
| 17 | 0.0113 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, headache, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipschotics and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL PART

Example 1 (Method A)

[1-(3-Methoxy-benzenesulfonyl)-piperidin-3-yl]-(2-phenyl-piperidin-1-yl)-methanone

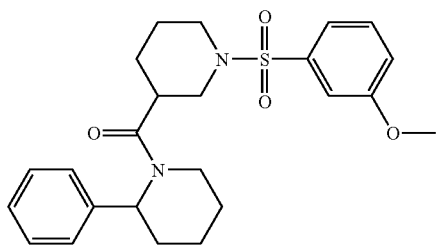

Step 1:

3-(2-Phenyl-piperidine-1-carbonyl)-piperidine-1-carboxylic acid tert.-butyl ester

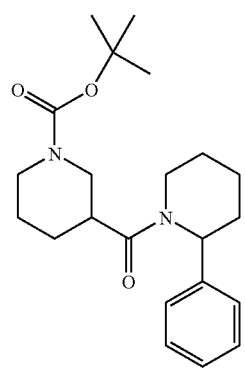

To a solution of 2 g of 1-(tert-butoxycarbonyl)-3-piperidinecarboxylic acid (commercially available) (8.72 mmol) in 15 mL of DMF: DCM (3:1) was added 1.39 g 2-phenylpiperidine (commercially available) (8.72 mmol) and 3.04 mL DIPEA (17.4 mmol). The mixture was stirred at room temperature for 10 minutes. 2.5 g EDCI (13.1 mmol) and 2.04 g HOBT (13.1 mmol) was added. The mixture was stirred for 6 h at room temperature, diluted with brine (50 mL) and extracted with ethyl acetate (2×40 mL). The combined organic layers were dried over sodium sulfate, filtered and evaporated at reduced pressure to obtain the crude product, which was further purified by column chromatography on silica eluting with 30-35% ethyl acetate in hexane to yield 1 g (31%) of the title compound. (MH+) 372.18.

Step 2:

(2-Phenyl-piperidin-1-yl)-piperidin-3-yl-methanone

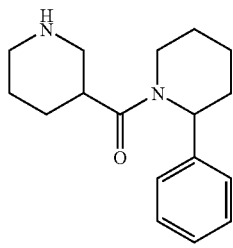

To a solution of 1 g 3-(2-phenyl-piperidine-1-carbonyl)-piperidine-1-carboxlic acid tert.-butyl ester in DCM (15 mL) was added 40% trifluoroacetic acid in DCM (6 mL). The mixture was stirred at room temperature for 4-5 h. After completion of the reaction all volatiles were evaporated, water (20 mL) was added and the mixture extracted with (2×25 mL) diethyl ether. The aqueous layer was adjusted with 10% aq. NaOH to pH=12, and extracted with ethyl acetate (2×25 mL). The combined organic layers were dried over sodium sulfate, filtered and evaporated under reduced pressure to yield 0.731 g (95%) of the title compound. (MH+) 273.36.

Step 3:

To a solution of 0.09 g of (2-phenyl-piperidine-1-yl)-piperidine-3-yl) methanone (0.33 mmol) and 0.2 mL DIPEA in DCM (5 mL) was added drop wise 0.082 g of 3-methoxy benzenesulfonyl chloride (0.39 mmol) at room temperature. The mixture was stirred at room temperature for 6 h. After completion of the reaction water (2×15 mL) was added. The organic layer was dried over anhydrous sodium sulfate, filtered and evaporated under reduced pressure to obtain the crude product which was further purified by column chromatography on silica eluting with 10-15% of ethyl acetate in hexane to yield 0.018 g (13%) of the title compound. (MH+) 443.35.

Example 2 (Method B)

[1-(2-Chloro-benzenesulfonyl)-piperidin-3-yl]-(2-m-tolyl-pyrrolidin-1-yl)-methanone

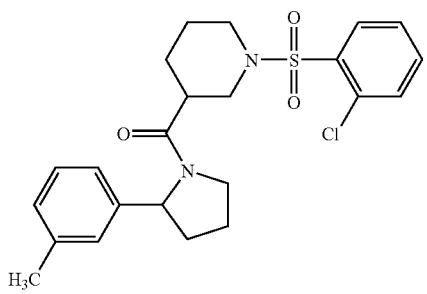

Step 1:

1-(2-Chloro-benzenesulfonyl)-piperidine-3-carboxylic acid ethyl ester

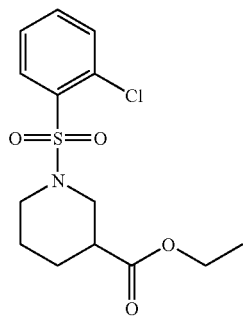

To a solution of 3.87 g piperidine-3-carboxylic acid ethyl ester hydrochloride (commercially available) (20 mmol) in 40 mL DCM was added 10 mL of DIPEA (60 mmol). At room temperature 2.72 mL 2-chloro-benzenesulfonyl chloride (20 mmol) was added drop wise and stirred for 14 h. The mixture was diluted with 30 mL of DCM, washed with water (3×50 mL) and the organic layer was dried over anhydrous sodium sulfate, filtered and evaporated under reduced pressure to obtain the crude product which was further purified by column chromatography on silica eluting with 10% ethyl acetate in hexane to yield 5.73 g (86.3%) of the title compound. (MH+) 332.16.

Step 2:

Lithium 1-(2-chloro-benzene sulfonyl)-piperidine-3 carboxylate

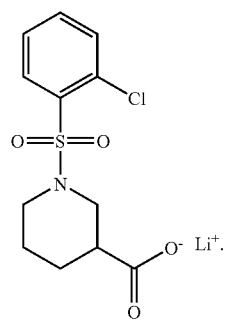

To a solution of 5.7 g 1-(2-chloro-benzenesulfonyl)-piperdine-3-carboxylic acid ethyl ester (17 mmol) in 30 mL THF: methanol: water (2:1:1) was added 1.08 g LiOH.H$_2$O (25.7 mmol). The mixture was stirred at room temperature for 5-6 h and all volatiles were evaporated to dryness. The compound was used in the consecutive step without further purification.

Step 3:

[1-(2-Chloro-benzenesulfonyl)-piperidin-3-yl]-(2-m-tolyl-pyrrolidin-1-yl)-methanone To a solution 0.1 g Lithium 1-(2-chloro-benzenesulfonyl)-piperidine-3-carboxylate (0.32 mmol) in DMF: DCM (3:1) was added 0.047 g 2-(3-methyl phenyl)-pyrrolidine (0.29 mmol) and 0.27 mL DIPEA (1.6 mmol). The mixture was stirred for 10 minutes at room temperature and 0.147 g HATU (0.38 mmol) was added. The mixture was stirred overnight at room temperature, diluted with 15 mL brine and extracted with ethyl acetate (3×10 mL). The combined organic layer was dried over anhydrous sodium sulfate, filtered and evaporated under reduced pressure to dryness to obtain the crude product which was further purified by column chromatography on silica eluting with 15% ethyl acetate in hexane to yield 0.03 g (20.8%) of the title compound. (MH+) 447.07.

In analogy to the procedures described for examples 1 and 2 further piperidine sulfonamide derivatives of examples 3-19 have been prepared with the method and from the starting materials as indicated in table 1.

TABLE 1

| No | structure | MW | Name | starting materials | Kb hOx2(uM) | MW found |
|----|-----------|------|------|-------------------|-------------|----------|
| 3 | 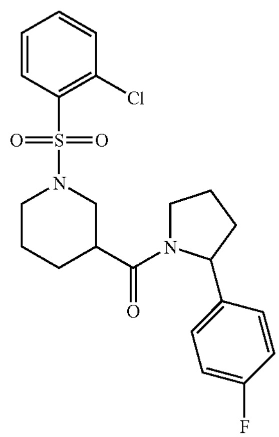 | 450.96 | [1-(2-Chloro-benzenesulfonyl)-piperidin-3-yl]-[2-(4-fluoro-phenyl)-pyrrolidin-1-yl]-methanone | Piperidine-3-carboxylic acid ethyl ester hydrochloride, 2-chloro-benzenesulfonyl chloride and 2-(4-fluoro-phenyl) pyrrolidine (commercially available) (method B) | 0.0788 | 451.16 |
| 4 | 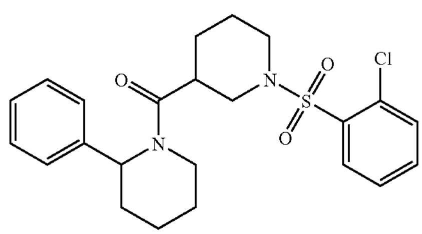 | 446.996 | [1-(2-Chloro-benzenesulfonyl)-piperidin-3-yl]-(2-phenyl-piperidin-1-yl)-methanone | 1-(tert-Butoxycarbonyl)-3-piperidinecarboxylic acid, 2-Phenyl-piperidine and 2-chloro-benzenesulfonyl chloride (all commercially available) (method A) | 0.1179 | 447.38 |
| 5 | 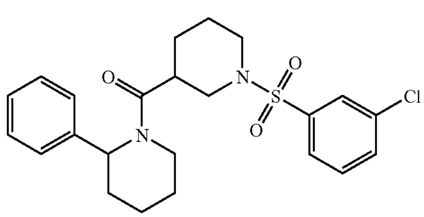 | 446.996 | [1-(3-Chloro-benzenesulfonyl)-piperidin-3-yl]-(2-phenyl-piperidin-1-yl)-methanone | 1-(tert-Butoxycarbonyl)-3-piperidinecarboxylic acid, 2-Phenyl-piperidine and 3-chloro-benzenesulfonyl chloride (all commercially available) (method A) | 0.5498 | 447.29 |
| 6 | 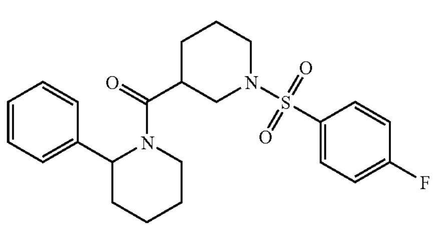 | 430.541 | [1-(4-Fluoro-benzenesulfonyl)-piperidin-3-yl]-(2-phenyl-piperidin-1-yl)-methanone | 1-(tert-Butoxycarbonyl)-3-piperidinecarboxylic acid, 2-Phenyl-piperidine and 4-fluorobenzenesulfonyl chloride (all commercially available) (method A) | 0.7562 | 431.34 |
| 7 | 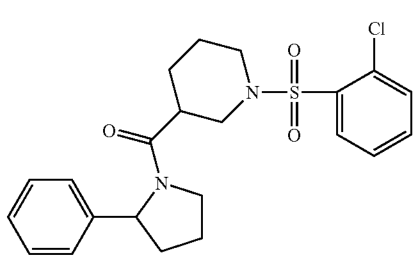 | 432.969 | [1-(2-Chloro-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 2-chloro-benzenesulfonyl chloride (all commercially available) (method A) | 0.02 | 433.29 |

TABLE 1-continued

| No | structure | MW | Name | starting materials | Kb hOx2(uM) | MW found |
|---|---|---|---|---|---|---|
| 8 | 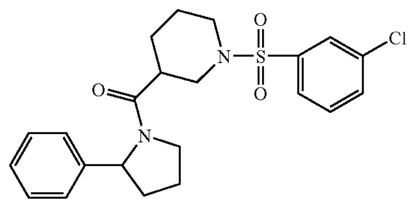 | 432.969 | [1-(3-Chloro-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 3-chloro-benzenesulfonyl chloride (all commercially available) (method A) | 0.0219 | 433.27 |
| 9 | 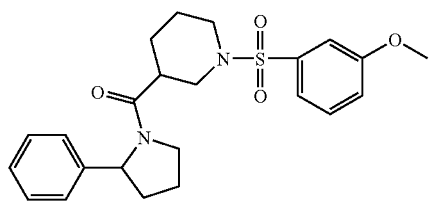 | 428.55 | [1-(3-Methoxy-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 3-methoxy-benzenesulfonyl chloride (all commercially available) (method A) | 0.1218 | 429.34 |
| 10 | 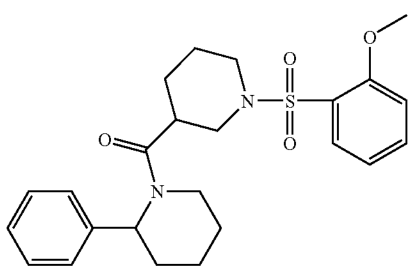 | 442.577 | [1-(2-Methoxy-benzenesulfonyl)-piperidin-3-yl]-(2-phenyl-piperidin-1-yl)-methanone | 1-(tert-Butoxycarbonyl)-3-piperidinecarboxylic acid, 2-Phenyl-piperidine and 2-methoxy-benzenesulfonyl chloride (all commercially available) (method A) | 0.0226 | 443.31 |
| 11 | 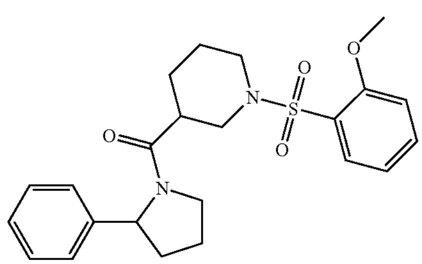 | 428.55 | [1-(2-Methoxy-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 2-methoxy-benzenesulfonyl chloride (all commercially available) (method A) | 0.0053 | 429.36 |
| 12 | 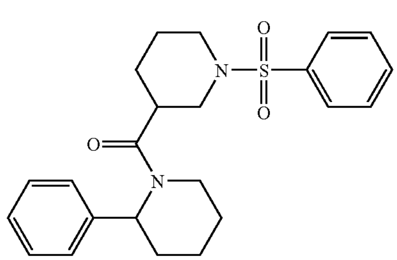 | 412.551 | (1-Benzenesulfonyl-piperidin-3-yl)-(2-phenyl-piperidin-1-yl)-methanone | 1-(tert-Butoxycarbonyl)-3-piperidinecarboxylic acid, 2-Phenyl-piperidine and benzenesulfonyl chloride (all commercially available) (method A) | 0.309 | 413.35 |
| 13 | 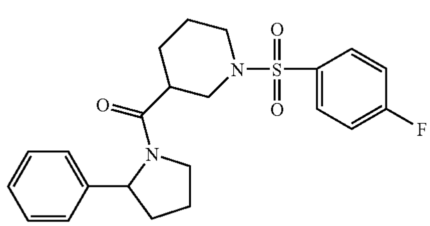 | 416.514 | [1-(4-Fluoro-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 4-fluoro-benzenesulfonyl chloride (all commercially available) (method A) | 0.3335 | 417.3 |

TABLE 1-continued

| No | structure | MW | Name | starting materials | Kb hOx2(uM) | MW found |
|---|---|---|---|---|---|---|
| 14 | 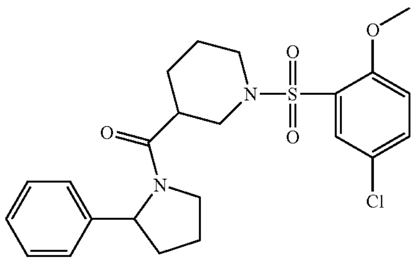 | 462.995 | [1-(5-Chloro-2-methoxy-benzenesulfonyl)-piperidin-3-yl]-(2-phenyl-pyrrolidin-1-yl)-methanone | 1-(tert-Butoxycarbonyl)-3-piperidinecarboxylic acid, 2-Phenyl-pyrrolidine and 5-chloro-2-methoxy-benzenesulfonyl chloride (all commercially available) (method A) | 0.0138 | 463.28 |
| 15 | 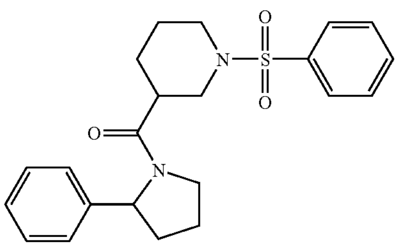 | 398.524 | (1-Benzenesulfonyl-piperidin-3-yl)-(2-phenyl-pyrrolidin-1-yl)-methanone | 1-(tert-Butoxycarbonyl)-3-piperidinecarboxylic acid, 2-Phenyl-pyrrolidine and benzenesulfonyl chloride (all commercially available) (method A) | 0.2579 | 399.33 |
| 16 | 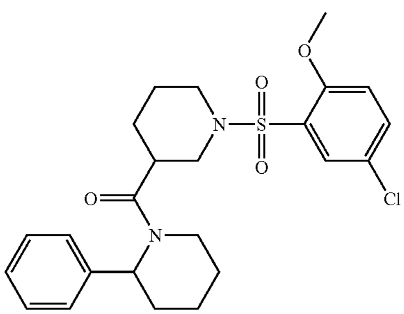 | 477.022 | [1-(5-Chloro-2-methoxy-benzenesulfonyl)-piperidin-3-yl]-(2-phenyl-piperidin-1-yl)-methanone | 1-(tert-Butoxycarbonyl)-3-piperidinecarboxylic acid, 2-Phenyl-piperidine and 5-chloro-2-methoxy-benzenesulfonyl chloride (all commercially available) (method A) | 0.0592 | 477.3 |
| 17 | 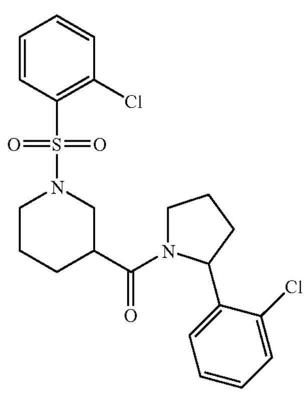 | 467.415 | [1-(2-Chloro-benzenesulfonyl)-piperidin-3-yl]-[2-(2-chloro-phenyl)-pyrrolidin-1-yl]-methanone | Piperidine-3-carboxylic acid ethyl ester hydrochloride, 2-chloro-benzenesulfonyl chloride and 2-(2-chloro-phenyl) pyrrolidine (commercially available) (method B) | 0.0113 | 467.75 |

TABLE 1-continued

| No | structure | MW | Name | starting materials | Kb hOx2(uM) | MW found |
|----|-----------|-----|------|-------------------|-------------|----------|
| 18 | 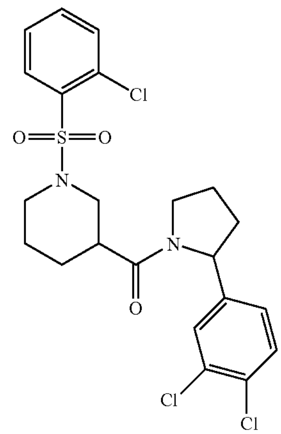 | 501.86 | [1-(2-Chloro-benzenesulfonyl)-piperidin-3-yl]-[2-(3,4-dichloro-phenyl)-pyrrolidin-1-yl]-methanone | Piperidine-3-carboxylic acid ethyl ester hydrochloride, 2-chloro-benzenesulfonyl chloride and 2-(3,4-dichloro-phenyl) pyrrolidine (commercially available) (method B) | 0.75 | 503.06 |
| 19 | 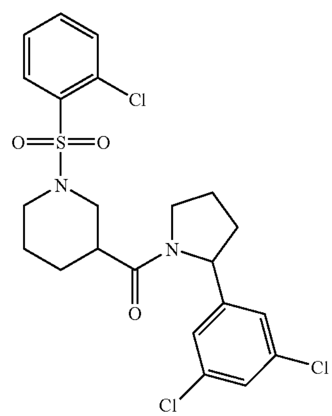 | 501.86 | [1-(2-Chloro-benzenesulfonyl)-piperidin-3-yl]-[2-(3,5-dichloro-phenyl)-pyrrolidin-1-yl]-methanone | Piperidine-3-carboxylic acid ethyl ester hydrochloride, 2-chloro-benzenesulfonyl chloride and 2-(3,5-dichloro-phenyl) pyrrolidine (commercially available) (method B) | 0.6697 | 503.06 |

The invention claimed is:

1. A compound of formula I

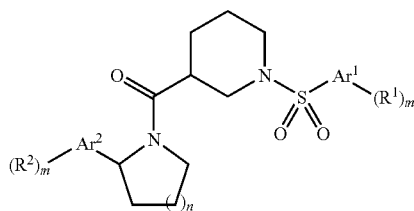

I wherein
Ar¹ and Ar² are each independently unsubstituted or substituted phenyl;
R¹ and R² are each independently hydroxy, halogen, lower alkyl, lower alkyl substituted by halogen, lower alkoxy, lower alkoxy substituted by halogen or cyano;
m is 0, 1, 2 or 3; and
n is 1;
or pharmaceutically suitable acid addition salts thereof.

2. The compound of claim 1, selected from the group consisting of

[1-(2-chloro-benzenesulfonyl)-piperidin-3-yl]-[2-(4-fluoro-phenyl)-pyrrolidin-1-yl]-methanone;

[1-(2-chloro-benzenesulfonyl)-piperidin-3-yl]-(2-phenyl-pyrrolidin-1-yl)-methanone;

[1-(3-chloro-benzenesulfonyl)-piperidin-3-yl]-(2-phenyl-pyrrolidin-1-yl)-methanone;

[1-(2-methoxy-benzenesulfonyl)-piperidin-3-yl]-(2-phenyl-pyrrolidin-1-yl)-methanone;

[1-(5-Chloro-2-methoxy-benzenesulfonyl)-pipendin-3-yl]-(2-phenyl-pyrrolidin-1-yl)-methanone; and

[1-(2-chloro-benzenesulfonyl)-pipendin-3-yl]-[2-(2-chloro-phenyl)-pyrrolidin-1-yl]-methanone.

3. The compound of claim 1, wherein m is 0.

4. The compound of claim 1, wherein m is 1.

5. The compound of claim 1, wherein m is 2.

6. The compound of claim 1, wherein m is 3.

7. A pharmaceutical composition comprising a compound of formula I

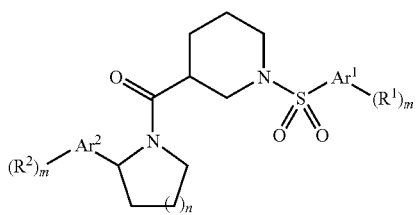
wherein
Ar¹ and Ar² are each independently unsubstituted or substituted phenyl;
R¹ and R² are each independently hydroxy, halogen, lower alkyl, lower alkyl substituted by halogen, lower alkoxy, lower alkoxy substituted by halogen or cyano;
m is 0, 1, 2 or 3; and
n is 1;
or pharmaceutically suitable acid addition salts thereof and a pharmaceutically acceptable carrier.
* * * * *